US008979266B2

(12) United States Patent
Cense et al.

(10) Patent No.: US 8,979,266 B2
(45) Date of Patent: Mar. 17, 2015

(54) DEVICES AND METHODS FOR POLARIZATION-SENSITIVE OPTICAL COHERENCE TOMOGRAPHY AND ADAPTIVE OPTICS

(75) Inventors: Abraham J. Cense, Utsunomiya (JP); Donald T. Miller, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 188 days.

(21) Appl. No.: 13/144,988

(22) PCT Filed: Jan. 22, 2010

(86) PCT No.: PCT/US2010/021759
§ 371 (c)(1),
(2), (4) Date: Oct. 7, 2011

(87) PCT Pub. No.: WO2010/085618
PCT Pub. Date: Jul. 29, 2010

(65) Prior Publication Data
US 2012/0038885 A1  Feb. 16, 2012

Related U.S. Application Data

(60) Provisional application No. 61/146,691, filed on Jan. 23, 2009.

(51) Int. Cl.
*A61B 3/14* (2006.01)
*A61B 3/10* (2006.01)
(Continued)

(52) U.S. Cl.
CPC ............... *A61B 3/102* (2013.01); *G01B 11/168* (2013.01); *A61B 3/1225* (2013.01)

USPC ........................................... 351/206; 356/492

(58) Field of Classification Search
CPC ................................... G01J 4/01; G01N 21/21
USPC ..................................... 351/206; 356/366, 492
See application file for complete search history.

(56) References Cited

U.S. PATENT DOCUMENTS 5,788,632 A * 8/1998 Pezzaniti et al. ............... 600/316
7,289,211 B1 * 10/2007 Walsh et al. ................... 356/369

(Continued)

OTHER PUBLICATIONS

Park et al. "Jones matrix analysis for a polarization-sensitive optical coherence tomography system using fiber-optic components," Nov. 1, 2004, OSA, Optics Letters, vol. 29, No. 21, pp. 2512-2514.*

*Primary Examiner* — Thomas K Pham
*Assistant Examiner* — Marin Pichler
(74) *Attorney, Agent, or Firm* — Ice Miller LLP

(57) ABSTRACT

The present disclosure includes disclosure of devices, and methods to resolve microscopic structures. In at least one exemplary embodiment, a visualization apparatus comprises a source arm having a light source operable to emit a light beam, wherein the light beam defines a beam pathway, a reference arm comprising a reflecting surface positioned within the beam pathway, a sample arm comprising a wavefront sensor, an adaptive optics wavefront corrector, and a target, each of which are positioned within the beam pathway, wherein the adaptive optics wavefront corrector is operable to compensate for at least one aberration in the light beam, a detector arm comprising a beam detector positioned within the beam pathway, wherein the beam detector is operable to detect the reflected light beam from the reference arm and the target, and wherein the visualization apparatus is operable to minimize at least one aberration of the target.

33 Claims, 8 Drawing Sheets

(51) Int. Cl.
*A61B 3/12* (2006.01)
*G01B 11/16* (2006.01)

(56) References Cited

U.S. PATENT DOCUMENTS

| | | |
|---|---|---|
| 2002/0091323 A1 | 7/2002 | Dreher |
| 2003/0220749 A1 | 11/2003 | Chen et al. |
| 2005/0007603 A1 | 1/2005 | Arieli et al. |
| 2005/0190373 A1 | 9/2005 | Pepper et al. |
| 2006/0044510 A1* | 3/2006 | Williams et al. ............. 351/221 |
| 2006/0058682 A1* | 3/2006 | Miller et al. ................. 600/476 |
| 2006/0169904 A1* | 8/2006 | Grobmyer et al. ......... 250/341.4 |
| 2006/0291849 A1* | 12/2006 | Shamir et al. ................ 396/334 |
| 2007/0030770 A1 | 2/2007 | Hirai |
| 2007/0263171 A1* | 11/2007 | Ferguson et al. ............ 351/206 |
| 2008/0007734 A1* | 1/2008 | Park et al. .................... 356/495 |
| 2008/0043226 A1* | 2/2008 | Hayashi et al. ................ 356/73 |
| 2008/0074644 A1 | 3/2008 | Levenson et al. |
| 2008/0231807 A1* | 9/2008 | Lacombe et al. ............. 351/215 |

* cited by examiner

DEVICES AND METHODS FOR POLARIZATION-SENSITIVE OPTICAL COHERENCE TOMOGRAPHY AND ADAPTIVE OPTICS

CROSS REFERENCE TO RELATED APPLICATION

The present application is a U.S. National Stage Application of International Patent Application PCT/US10/21759, titled "DEVICES AND METHODS FOR POLARIZATION-SENSITIVE OPTICAL COHERENCE TOMOGRAPHY AND ADAPTIVE OPTICS," filed Jan. 22, 2010, which claims priority to U.S. Provisional Patent Application Ser. No. 61/146,691, filed on Jan. 23, 2009, the contents of which are incorporated herein by reference.

STATEMENT REGARDING FEDERALLY SPONSORED RESEARCH

The work leading to the invention received support from the United States federal government under National Eye Institute Grant Nos. EY014743, and EY018339, as well as National Science Foundation Grant No. AST-9876783. The federal government has certain rights in the invention.

BACKGROUND

Optical coherence tomography (OCT) has established itself as a non-contact method for retinal imaging. OCT has a higher axial resolution than other retinal imaging methods such as scanning laser ophthalmoscopy and fundus imaging. High sensitivity, axial resolution, and speed are important attributes for probing the retina at the cellular level. While the axial resolution (z-direction) using OCT can be up to 3 µm in retinal tissue, the lateral resolution (xy-direction) of retinal imaging systems is typically reported to be at best 15 µm due to the aperture of the eye, and presence of ocular aberrations. With the introduction of spectral-domain OCT (SD-OCT) for retinal imaging, retinal tomograms may be made at video rate, without loss of sensitivity or resolution.

Advances in OCT have allowed for the detection of polarization properties of layers within the retina. The devices which have capacity for polarization detection are referred to as polarization-sensitive optical coherence tomography (PS-OCT) devices. Additional detail on PS-OCT may be seen in United States Patent Application publication number 2007/0038040, which is incorporated herein by reference. Layers of the retina which are known to have distinct polarization properties include the birefringent nerve fiber layer and Henle's fiber layer, diattenuating photoreceptor layer, and depolarizing retinal pigment epithelium. Additionally, polarization changes are proposed to be a sensitive indicator of cellular health. Further, it is thought that diseases of the eye such as glaucoma and age-related macular degeneration may be diagnosed and assayed based on the polarization properties of retinal cells. The level of resolution possessed by PS-OCT currently though, is inadequate for visualizing the polarization properties of cell types associated with these diseases.

Adaptive Optics (AO) is a technology used to improve the performance of optical systems by reducing the effects of optical aberrations. This improved performance is generated by measuring the aberrations in a wavefront and compensating for them with a spatial phase modulator, sometimes called a wavefront corrector or deformable mirror.

Therefore, since current apparatuses cannot detect many important microscopic structures, such as individual retinal cells, it is desirable to have a PS-OCT system which is capable of resolution better than 15 µm. Production of such a system would facilitate the visualization of structures associated with the formation or presence of various retinal conditions, such as glaucoma and age-related macular degeneration.

SUMMARY

According to at least one embodiment of a visualization apparatus, the apparatus comprises a source arm comprising a light source operable to emit a light beam, wherein the light beam defines a beam pathway, a reference arm comprising a reflecting surface positioned within the beam pathway and capable of reflecting the light beam, a sample arm comprising a wavefront sensor, an adaptive optics wavefront corrector, and a target, wherein each of the wavefront sensor, the adaptive optics wavefront corrector, and the target are positioned within the beam pathway, wherein the adaptive optics wavefront corrector is operable to compensate for at least one aberration in the light beam, a detector arm comprising a beam detector positioned within the beam pathway, wherein the beam detector is operable to detect the reflected light beam from the reference arm and light beam returning from the target, wherein the visualization apparatus is operable to minimize at least one aberration from an optical element or the target.

The adaptive optics wavefront compensator comprises, in at least one embodiment, an array of actuators. The array of actuators, of at least one embodiment of a visualization apparatus, is selected from a group of about 20 or more, about 37 or more, about 100 or more, and about 144 or more piezoelectric actuators. Further, the array of actuators may be capable of adjusting the shape of the deformable mirror by at least 2 microns, or at least 5 microns. In at least one embodiment, the adaptive optics wavefront corrector diminishes at least one aberation produced by the target.

Additionally, at least one embodiment of the visualization apparatus further comprises a beam splitter operably coupled to the source arm, the reference arm, the sample arm, and the detector arm, wherein the beam splitter is capable of shunting a first portion of the light beam to the reference arm and a second portion of the light beam to the sample arm, wherein the first portion of the light beam returning from the reference arm and the second portion of the light beam returning from the sample arm are directed by way of the beam splitter to the detector arm.

In at least one embodiment, the visualization apparatus may further comprise one or more of a calibration mechanism, an isolator, and a polarization modulator. The calibration mechanism is positioned within the beam pathway and operable to calibrate the light beam. The isolator is operable to prevent reflections of the light beam from interacting with the light source. Further, in at least one embodiment, the beam detector is synchronized with the polizarization modulator. Moreover, an exemplary embodiment of the visualization apparatus may additionally comprise a processor, wherein the processor is operably coupled to the beam detector.

In at least one embodiment of the visualization apparatus, the sample arm further comprises a first dichroic beam splitter in the beam pathway, a second dichroic beam splitter in the beam pathway, and a beacon operable to emit a beacon light in the beam pathway after the first dichroic beam splitter.

According to at least one embodiment of a visualization method, the method comprises measuring the at least one aberration in a target with an embodiment of the visualization apparatus as described herein, controlling the at least one aberration with the adaptive optics wavefront corrector to correct for the at least one aberration, detecting the corrected light beam with the detector arm, and analyzing the detected light beam with a processor. Additionally, in an embodiment of the method, the step of analyzing the detected light beam eliminates birefringence and scattering proterties of the target. Further, the step of analyzing the detected light, in at least one embodiment, comprises the steps of accumulating stokes vectors, averaging the stokes vectors with re-alignment of the stokes vectors using a moving average filter to produce an averaged data set, and transmission of the averaged data set to an additional process, a storage medium, or a display medium. Lastly, the method, according to at least one embodiment, may further comprise the step of displaying an image processed by the processor of the visualization apparatus by a display mechanism.

DETAILED DESCRIPTION

Devices and methods of the disclosure of the present application include apparatus for the detection of polarization properties of microscopic structures and methods of use of at least one embodiment of the apparatus. According to at least one embodiment of the apparatus, a polarization-specific optical coherence tomography (PS-OCT) device is modified to incorporate Adaptive Optics (AO) for the increased resolution of microscopic structures.

Figure 1:
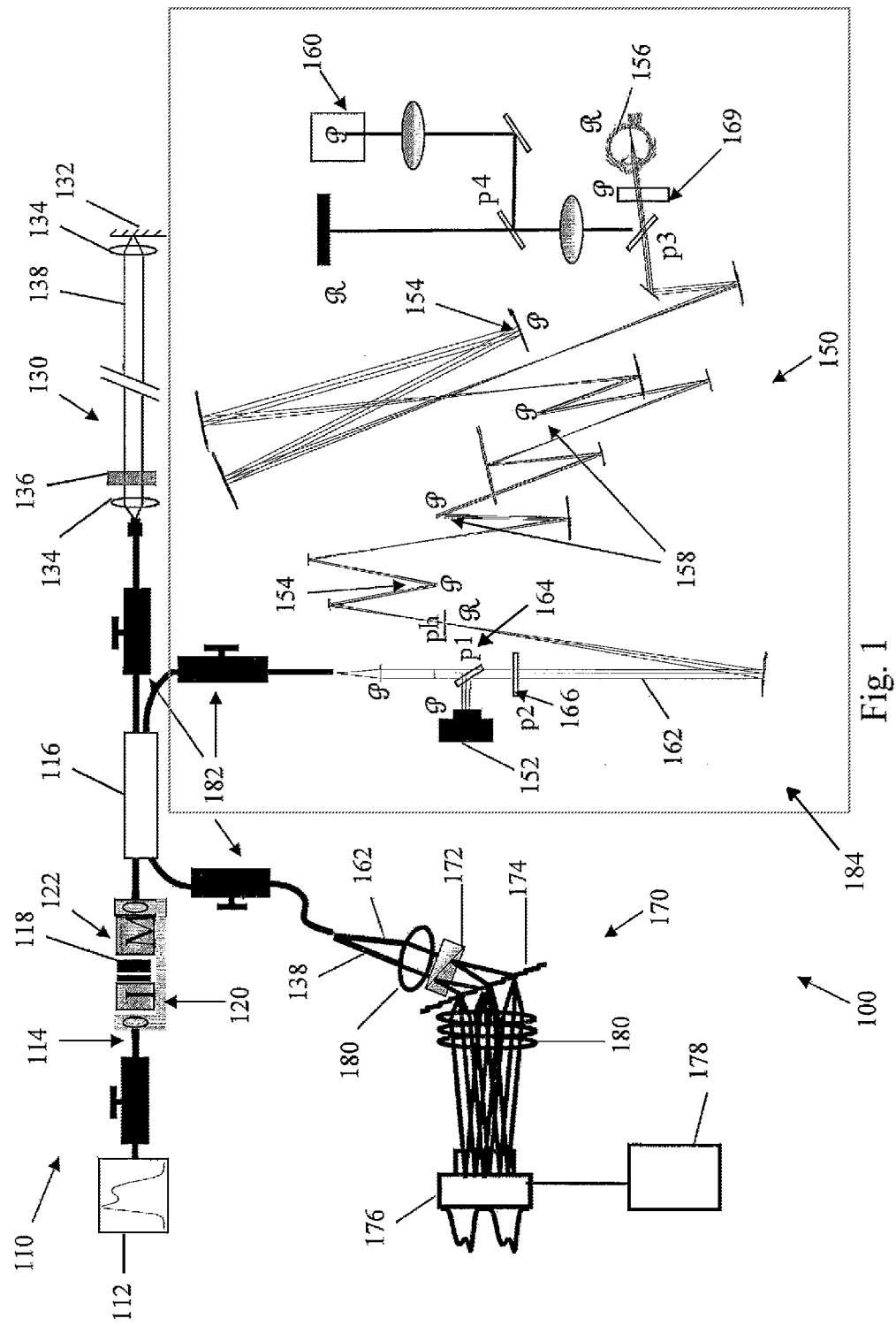
FIG. 1 shows a diagram of at least one embodiment of an apparatus of the present disclosure.

Turning towards FIG. 1, at least one embodiment of the AO PS-OCT apparatus 100 is described. The AO-PS-OCT apparatus 100 is comprised of source arm 110, reference arm 130, sample arm 150, and detector arm 170. Source arm 110 comprises a light source 112, which is operable to emit light beam 114 into reference arm 130 and sample arm 150. In at least one embodiment, beam 114 may be a single mode fiber, and beam splitter 116 may be a fiber coupler. In at least one embodiment light source 112 comprises a superluminescent diode. Beam splitter 116 in at least one embodiment may comprise a fiber coupler. The fiber coupler may serve to divide the power output of light beam 114 at a set ratio between reference arm 130 and sample arm 150 to form reference beam 138 and sample beam 162 respectively.

Light beam 114 may interact with a beam splitter 116 prior to entering reference arm 130 and sample arm 150. Beam splitter 116 may divide light beam 114 so that a certain percentage of beam 114 (e.g., at least about 90%, at least about 80%, at least about 70%, at least about 60%, at least about 50%, at least about 40% or at least about 30%) interacts with reference arm 130 as reference beam 138, and a certain percentage of beam 114 (e.g., at least about 70%, at least about 60%, at least about 50%, at least about 40%, at least about 30%, at least about 20%, or at least about 10%) interacts with sample arm 150 as reference beam 162.

Light Source 112, of AO-PS-OCT apparatus 100, can be any light source that is capable of providing light with a short coherence length, including, for example, white light sources (e.g. halogen sources, arc lampts, or flashlamps), semiconductor sources (e.g., SLD, light emitting diodes, doped fiber sources, multiple quantum well semiconductor optical amplifiers), solid state lasers (e.g., femtosecond lasers), spectrally-swept sources, or supercontinuum sources.

Source arm 110 may further comprise one or more additional elements, including calibration mechanism 118, isolator 120, and/or a polarization modulator 122. Calibration mechanism 118 may comprise a transparent material that serves to calibrate light beam 114 in an exemplary embodiment. The isolator 120 can protect the light source from reflections returning from the AO-PS-OCT apparatus 100. Polarization modulator 122 can act to ensure that an equal amount of power was transmitted to both states.

Reference arm 130 in at least one embodiment is comprised of a reflecting surface 132 which is positioned to interact with reference beam 138. Optionally, reflecting arm 130 may further comprise at least one lens 134, and/or a polarizer 136.

Figure 4:
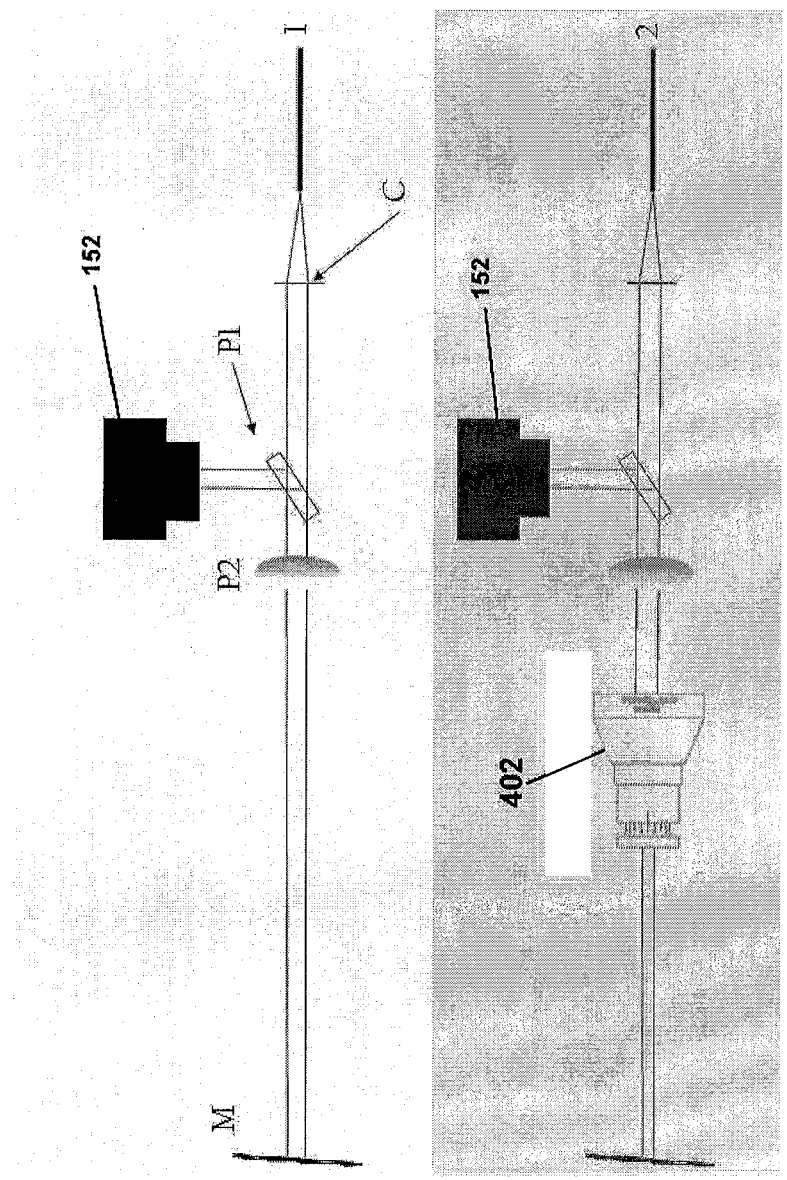
FIG. 4 shows at least one embodiment of a beam expander of the present disclosure.

Sample arm 150 in at least one embodiment is comprised of a wavefront sensor 152, an adaptive optics wavefront corrector 154, and a target 156. In at least one embodiment, wavefront sensor 152 may comprise a Hartmann-Shack wavefront sensor. Optionally, the wavefront sensor may comprise one of many other sensors, such as a phase-shifting interferometer, shearing interferometer, pyramid sensor, curvature sensor, laser ray tracing, even a single photodetector, which can be used in a wavefront sensorless adaptive optics system. Further, sample arm 150 may also comprise a first pellicle (p1) 164 positioned within the beam pathway. Lastly, sample arm 150 may further comprise a beam expander 402 (as shown in FIG. 4) positioned within sample beam 162.

Target 156 of the AO-PS-OCT apparatus 100, in an exemplary embodiment, may be any suitable biological tissue. The biological tissued examined may be, for example, an eye, or a portion of an eye (e.g., retinal tissue, fundus tissue, a cornea or crystalline lens of an eye).

Adaptive optics wavefront corrector 154 can be in any suitable form. For example, adaptive optics wavefront corrector 154 may be a deformable mirror that comprises a flexible mirror material bound to an array of actuators. The actuators function to adjust the shape of the mirror to within +/−2 microns or more (e.g., within +/−5 microns or more). Such actuators may be piezo-electric materials, for example, PZT (lead zirconate titanate), PLZT (lead lanthanide zirconate titanate), PFN (lead iron niobate), PMW (lead magnesium tunstate), PNN (lead nickel niobate), PMN (lead magnesium niobate), or doped PMN materials. Adaptive optics wavefront corrector 154 also can be a bimorph mirror containing two piezoelectric materials that are bonded together and oppositely polarized, a membrane mirror such as a continuous membrane deformable mirror (CMDM), a liquid crystal spatial light modulator (LC-SLM), or a micro-opto-electro-mechanical system (MOEMS, i.e., a micro-mirror). Further, the adaptive optics wavefront corrector 154 may comprise a flexible glass material that is coated with aluminum and having a plurality of piezo-electric actuators (e.g., about 20 or more, such as a 37-actuator Aoptix mirror, or a 144-element BMC deformable mirror). LC-SLMs and MOEMS in particular have the potential to be small and inexpensive.

In an additional embodiment of the sample arm 150, the sample arm 150 further comprises a second pellicle (p2) 166 positioned after first pellicle 164 and in the beam pathway. In a further embodiment of sample arm 150, sample arm 150 comprises a low-diattenuating beamsplitter 164, such as a polka dot beamsplitter or beamsplitter oriented at a small angle to the incident beam. In an additional embodiment, sample arm 150 may further comprise at least one galvanometer scanner 158. Further, in an additional embodiment, sample arm 150 may further comprise a scanner mechanism 160. Scanner mechanism 160 may in at least one embodiment be operable to visualize the pupil of an individual. In at least one embodiment, adaptive optics wavefront corrector 154 is operable to diminish the wavefront aberrations of sample beam 162.

Detector arm 170 is comprised of a prism 172, a transmission grating 174, and a beam detector 176. Additionally, detector arm 170 may further comprise at least one lens 180 that is capable of interacting with reference beam 138 and/or sample beam 162. In at least one embodiment, the components of detector arm 170 are positioned such that reference beam 138, and sample beam 162 each interact with prism 172, prior to interacting with transmission grating 176. Subsequently, reference beam 138 and sample beam 162 may be focused by lens 180 prior to being detected by beam detector 176. In at least one embodiment, prism 172 is any device or object which manipulates polarized light. Further, in at least one embodiment, prism 172 is be a Wollaston prism. Moreover, detector arm 170, as well as reference arm 130 and sample arm 150, may have a polarization controller 182.

Beam detector 176 can be in any suitable form, including both 1D and 2D detectors. For example, beam detector 176 can be a CCD array camera, an intensified CCD array camera, a Complementary Metal-Oxide Semiconductor (CMOS) array camera, a photodiode, a photodiode array, or an active pixel array (e.g., a photodiode array with electronics that perform heterodyned detection and demodulation by means of mixing and/or combined filtering and rectifying for recoveringsample phase and intensity, and beat frequency information). Such a photodiode array or active pixel array can be 1D or 2D. When light source 112 is a flood illumination light source, detector 176 may be a CCD array or an active pixel array. When light source 112 is a scanning point light source, detector 176 may be a photodiode or a photodiode array. Additionally, beam detector 176 may be synchronized with polarization modulator 122 in at least one embodiment. Further, processor 178, in at least one embodiment, is operably connected to beam detector 176.

Figure 2:
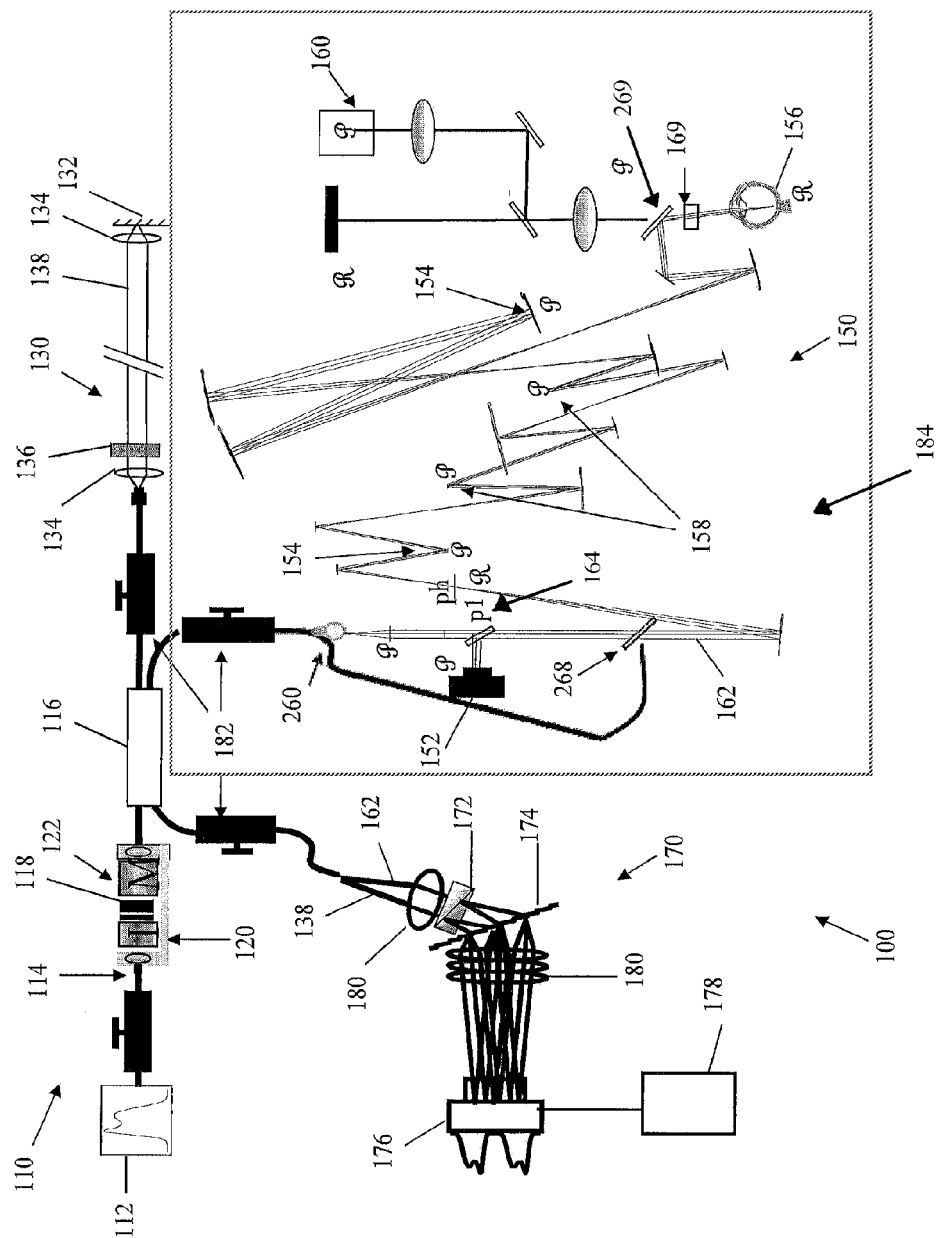
FIG. 2 shows a diagram of at least one embodiment of an apparatus of the present disclosure.

Turning towards FIG. 2, at least one additional embodiment of AO-PS-OCT apparatus 100 is shown. Components of AO-PS-OCT apparatus 100 may be those of any embodiment described above. Additionally, sample arm 150 may also comprise a first dichroic beam splitter 268 positioned in the beam pathway prior to adaptive optics wavefront corrector 154. Additionally, a second dichroic beam splitter 269 may be situated in the beam pathway between adaptive optics wavefront corrector 154 and target 156. Further, sample arm 150 may also comprise a beacon 260 positioned so that light from beacon 260 is introduced into sample arm 150 in the beam pathway after first dichroic beam splitter 268.

Figure 3:
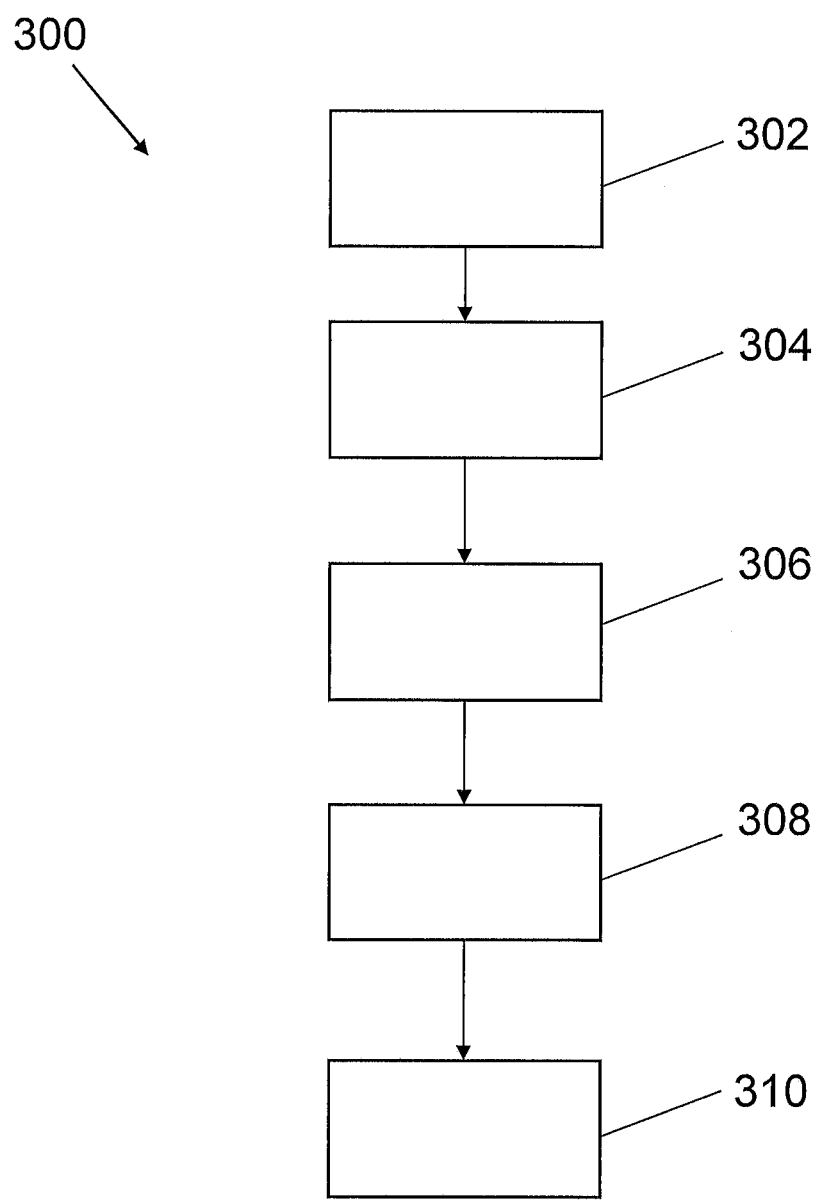
FIG. 3 shows a flowchart of at least one embodiment of a method of the present disclosure.

At least one embodiment of a method for visualization of structures using an embodiment of AO-PS-OCT apparatus 100 as described above, and as shown in FIG. 3, is detailed herein. In an exemplary embodiment of the method, the method comprises the steps of measuring 302 the at least one aberration in a target 156 with an embodiment of a visualization apparatus 100 as described herein, controlling 304 the at least one aberration determined by the visualization apparatus 100 with the adaptive optics wavefront corrector 154 to correct for the at least one aberration, detecting 306 the corrected light beam with the detector arm 170, and analyzing 308 the detected light beam with a processor 178.

In at least one embodiment of the method, beam 114 is emitted by light source 112 and travels beam splitter 116. Upon interacting with beam splitter 116, beam 114 is divided so that a certain percentage of beam 114 (as described above) may interact with reference arm 130 as reference beam 138, and a certain percentage of beam 114 (as described above) may interact with sample arm 150 as reference beam 162. Optionally, beam 114 may first interact with calibration mechanism 118 prior to beam splitter 116 to calibrate the beam 114. The calibration of beam 114, in at least one embodiment, is described in United States Patent Application 2007/0038040 to Cense which is incorporated herein by reference.

Upon entering reference arm 130, reference beam 138 strikes reflecting surface 132 and is reflected back towards beam splitter 116. Optionally, reference beam 138 may be focused by at least one lens 134 prior to striking reflecting surface 132. Further, reference beam 138 may be manipulated by polarizer 136 prior to striking reflecting surface 132. Following the reflection of reference beam 138 back to beam splitter 116, reference beam 138 is shunted towards detector arm 170.

Once entering sample arm 150, sample beam 162 interacts with pellicle 164 which directs sample beam 162 to wavefront sensor 152. Following detection by wavefront sensor 152, sample beam 162 is directed back to pellicle 164, followed by a second pellicle 166, and subsequently interacts with an adaptive optics wavefront corrector 154 and lastly with target 156 before reflecting along the same path. The interaction of sample beam 162 with adaptive optics wavefront corrector 154 may in at least one embodiment alter the wavefront of sample beam 162 so as to correct for the wavefront aberrations. Following the interaction with target 156, sample beam 162 interacts with beam splitter 116 which directs sample beam 162 to detector arm 170.

In an additional embodiment (see FIG. 2), once entering sample arm 150, sample beam 162 interacts with a first dichroic beam splitter 268, followed by an interaction with an adaptive optics wavefront corrector 154, and subsequently a second dichroic beam splitter 269 prior to interacting with target 156 before reflecting along the same path. Adaptive optics may be performed with a beacon 260, which traverses pellicle 164 and dichroic beam splitter 268. All light from sample beam 162 and from beacon 260 reflects from dichroic beam splitter 269 into target 156. Reflections occur along the same path before the sample beam 162 returning from the eye is reflected back into the interferometer. The beacon light returning from the target 156 traverses dichroic beam splitter 268 after which a certain percentage of the light is reflected towards wavefront sensor 152.

Reference beam 138 and sample beam 162 each traverse prism 172 following entry into detector arm 170. Following the traversing of prism 172, reference beam 138 and sample beam 162 interact with transmission grating 174, followed by lens 180 prior to being detected 306 by beam detector 176. Once reference beam 138 and sample beam 162 are detected by beam detector 176, processor 180, which is operably coupled to beam detector 176, acts to analyze 308 the data generated by beam detector 176 and resolve the image and eliminate birefringence and scattering properties of target 156. Additionally, in at least one embodiment, beam detector may be synchronized with polarization modulator 122. Lastly, in an exemplary embodiment, the method further comprises the step of displaying 310 an image processed by the processor of the visualization apparatus with a display mechanism.

According to at least one embodiment, the analysis 308 by processor 180 of the data generated by beam detector 176 occurs through the process that involves (1) the accumulation of Stokes vectors, (2) the averaging of the stokes vectors with re-alignment of the stokes vectors using a moving average filter to produce an averaged data set, and (3) transmission of the averaged data set to an additional process, storage medium, or display medium. Previously this phase difference has been analyzed with realignment with respect to the surface of the retina, prior to Stokes vector averaging, which is necessary to reduce the influence of speckle noise. Then, the averaged data was shifted back to its original position, using the earlier determined location of the surface. The problem was that pixels were averaged that were originally not adjacent to each other, creating artifacts. Processing of the Stokes data with re-alignment does not allow for the resolving of the Stokes vectors to diminish the effects of phase noise caused by speckle, since it adds artifacts.

According to an embodiment, Jones matrix calculations may be used to retrieve polarization properties such as phase retardation, diattenuation and fast axis orientation. Prior to these calculations, the data has to be acquired in such a way that Jones matrix calculations are possible, such as the use of a resonant polarization modulator 122 in the source arm. An advantage of this combination is that the diattenuation of tissue can be measured with high spatial accuracy, which can be important for measurements on tissue with diattenuating properties. At least one application of AO-PS-OCT apparatus 100 is functional imaging with AO-PS-OCT, for instance to measure the effect of light on diattenuation in cone photoreceptors, as described by Weale (R. A. Weale, "Optical properties of photoreceptors," Br. Med. Bull. 26, 134-137 (1970).)

In another embodiment, polarization-maintaining fiber is used throughout the interferometer, and the polarization state at the pupil of the eye is maintained circular with a quarter waveplate 169, ensuring interaction between the incident polarization state and the birefringent tissue in the retina. Furthermore, an embodiment of this method allows phase retardation and fast axis orientation determination using a single A-scan (depth scan), which will give phase retardation and fast axis orientation images that are less sensitive to shot noise, and will therefore be more accurate. (See Al-Quasi et al (M. K. Al-Qaisi, and T. Akkin, "Polarization-sensitive optical coherence tomography based on polarization-maintaining fibers and frequency multiplexing," Optics Express 16, 13032-13041 (2008)).

In a further embodiment, the interferometer is made from bulk elements, and the polarization state at the pupil of the eye is maintained with a quarter waveplate 169. (See Gotzinger et al. (E. Gotzinger, M. Pircher, R. A. Leitgeb, and C. K. Hitzenberger, "High speed full range complex spectral domain optical coherence tomography," Optics Express 13, 583-594 (2005)).

According to at least one embodiment, the AO-PS-OCT system is used in combination with an ultrabroadband source ($\Delta\lambda > 100$ nm) to reduce the speckle length in depth. Over a similar depth, more speckles can be averaged using the ultrabroadband source, compared to a standard source. The averaging of multiple speckles leads to a more reliable orientation determination of the Stokes vector elements, thereby improving the accuracy with which the phase retardation and fast axis orientation are determined.

Inclusion of AO with PS-OCT offers three distinct advantages for PS-OCT measurements: an increased signal-to-noise ratio (which leads to a more reliable detection of Stokes vectors), a higher lateral resolution and a smaller speckle size. PS-OCT measurements with AO (6 mm beam) were compared to measurements in a standard setup, without AO (1.2 mm beam), on the same subject at the same location.

EXAMPLES

Example 1

An adaptive optics OCT system has been developed with polarization-sensitive technology around a single line scan camera spectrometer with a Wollaston prism (see FIG. 1). FIG. 1 shows an embodiment for polarization-sensitive OCT with adaptive optics. Included in FIG. 1 are elements: superluminescent diode; I: isolator; M: polarization modulator; p1-p4: pellicle beam splitters; ph: pinhole; and 𝒫/ℛ: relevant pupil and retinal planes. In the source arm, light from a superluminescent diode (Superlum HP-371, $\Delta\lambda_{FWHM}=50$ nm, $\lambda_c=840$ nm, P=10 mW) was modulated at 13.1 kHz into two polarization states, orthogonal in the Poincaré sphere. As an example, linearly polarized light (independent of the angle of polarization) and circularly polarized light are 90° apart on the Poincaré sphere. The detection scheme is insensitive to corneal birefringence and birefringence in the system, for instance due to stress in the single mode fiber, because it uses the retinal surface as a reference. The system was calibrated with two microscope slides with different thicknesses in the source arm. The superluminescent diode was protected from reflections returning from the system with an optical isolator. An 80/20 fiber-coupler sent 80% of the power towards the reference arm, while 20% of the power was sent towards the sample arm. The reference and sample arm lengths were matched in optical path length distance and second order chromatic dispersion was minimized with a reference arm water vial. Remaining chromatic dispersion was compensated with software. The reference arm also contained a linear polarizer to ensure that an equal amount of power was transmitted for both polarization states.

In the sample arm, multiple flat and spherical mirrors were used to conjugate the pupil planes of a Shack-Hartmann wave front sensor (SHWS), two deformable mirrors, two galvanometer scanners, and the pupil of the eye. The total transmission loss of this sample arm that contained 18 optical elements measured with a broadband power meter (Ophir)

was equal to 48% in single pass. Low order aberrations in cornea and lens were corrected by means of a 37-actuator Aoptix bimorph mirror, which also permits to focus at different layers in the retina. A 144-element BMC deformable mirror was used to correct higher order aberrations. The central 10×10 elements were illuminated. The woofer-tweeter design with the large stroke Aoptix mirror permits measurements on subjects that need large amounts of correction (cylinder, sphere) without use of trial lenses.

Since pellicle 3 (p3) was removed directly before an experiment to avoid diattenuation, a small movable light source in the system itself was used as a fixation target. When the fixation target was blocked by optical components in the system, the co-lateral eye was used for fixation. The target's head was positioned in a head rest and bite bar setup to minimize head motion. The right eye of the target was dilated by means of hourly drops of 1% tropicamide and 2.5% phenylephrine. B-scans were either 1° (~300 µm), or 3° (~900 µm) long and taken at 1° and 3° eccentricity from the fovea.

Light returning from sample and reference arm was detected by means of a polarization-sensitive high-speed spectrometer. A Wollaston prism with a 6° separation angle was used to separate two orthogonal states next to each other on a single line scan camera (Atmel SM 2048). The center 1400 detector elements of this 2048 element camera with 14×14 µm detector elements were used, with the two orthogonal states illuminating 700 elements each (1400 elements total). The Wollaston prism was positioned after the collimator and as close as possible to the transmission grating, which allowed us to use a significantly smaller and cheaper Wollaston prism with a length and width of only 10 mm.

The line scan camera was synchronized with the polarization modulator. Data was acquired at 26,300 A-lines/s and the integration time for one A-scan was equal to 32 µs. The efficiency of the spectrometer was estimated at 21-24%, using noise analysis. Measurements on a mirror positioned at different optical path length differences did not show a significant difference in decay between the two polarization states. This result shows that the spectrometer detects phase retardation accurately and that the system is free of birefringence artifacts.

In conventional OCT without AO, a pupil of approximately 1 to 2 mm is chosen, since this size offers the best balance between a diffraction limited spot and corneal aberrations. Other groups involved with PS-OCT for retinal imaging use a beam smaller than 1 mm, or a 3.5 mm beam. Previously, other groups have found that a diameter of 1.22 mm (at 570 nm) offers an optimal balance.

Example 2

Implementation of an inverted 5x beam expander in shown in FIG. 4 to reduce the beam width. C: collimator; SHWS: Shack-Hartmann wavefront sensor; M: mirror; P1 and P2: pellicle beam splitters. To make a fair comparison in a PS-OCT system with and without AO, a 5X beam expander was put in a collimated beam, closely to the collimator (see FIG. 4). The beam diameter at this location was reduced by a factor of five from 10 mm down to 2 mm After magnification through the system, the 1/e2 beam diameter at the eye's pupil was equal to 1.2 mm. For the 1.2 mm pupil we expect a diffraction limited Airy disk at the retina with a diameter of 14.1 µm. In contrast, the 6.0 mm pupil setting creates a theoretical Airy disk on the retina of 3.1 µm. In the return path the full 6.0 mm pupil is used to collect reflected light, which benefits the SNR. Due to a more efficient collection, and assuming a Gaussian distribution, one expects to gain a 17.7 times improvement, or 12.5 dB. The difference in SNR between the two systems was quantified, while the speckle size in the retina was compared using an auto-correlation method.

To determine the performance of the woofer-tweeter design, a subject with −4.75 D of sphere was imaged with the system without the use of trial lenses. OCT data was recorded for 10 s. First, the loop for the Aoptix mirror was closed until equilibrium and held, subsequently followed by a closing the loop for the BMC mirror. The performance of the adaptive optics system was quantified by analyzing the SHWS data and OCT data.

Example 3

Figure 5:
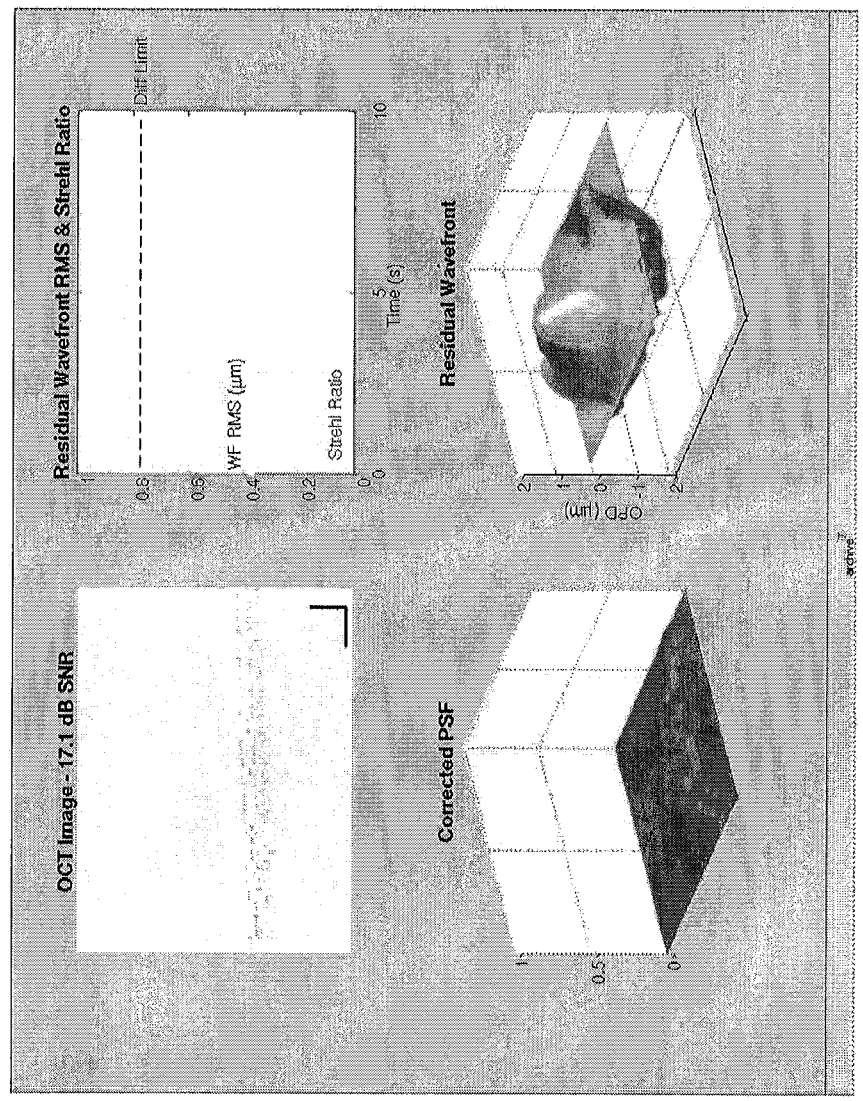
FIG. 5 shows the results of an assay to determine the performance of an embodiment of an apparatus according to FIG. 1.

FIG. 5 contains a depiction of the performance of the woofer-tweeter system on a 29-year old subject with a prescription of −4.75 D of sphere. At t=0 s, the deformable mirrors were in system flat mode. After approximately 2 s, the Aoptix mirror was switched on, improving the Strehl ratio to approximately 0.12 and reducing the residual wavefront RMS to approximately 0.25 µm RMS. Note that since not all centroids on the Shack-Hartmann wavefront sensor were filled during the first ~3 seconds due to large aberrations, the values for residual wavefront RMS, Strehl ratio and corrected PSF are incorrect. A sphere value of −4.75 diopters causes a wavefront RMS of approximately 3.5 µm RMS, well outside the graph. When the loop for the Aoptix mirror stabilizes around t=~6 s, the mirror is held in the same position after which the loop for the BMC deformable mirror is closed (t=~7 s). The wavefront RMS reduces to less than 0.1 and the Strehl ratio improves to more than 0.8, indicating a diffraction limited performance. The residual wavefront has become nearly flat at this point in time. The dynamic range within the OCT image improves from 17 dB at the start to more than 40 dB in the last frames, an increase of more than 20 dB or 100 times, demonstrating that this woofer-tweeter system can correct for the aberrations in a 29-year old subject with −4.75 D of sphere.

Example 4

Figure 6:
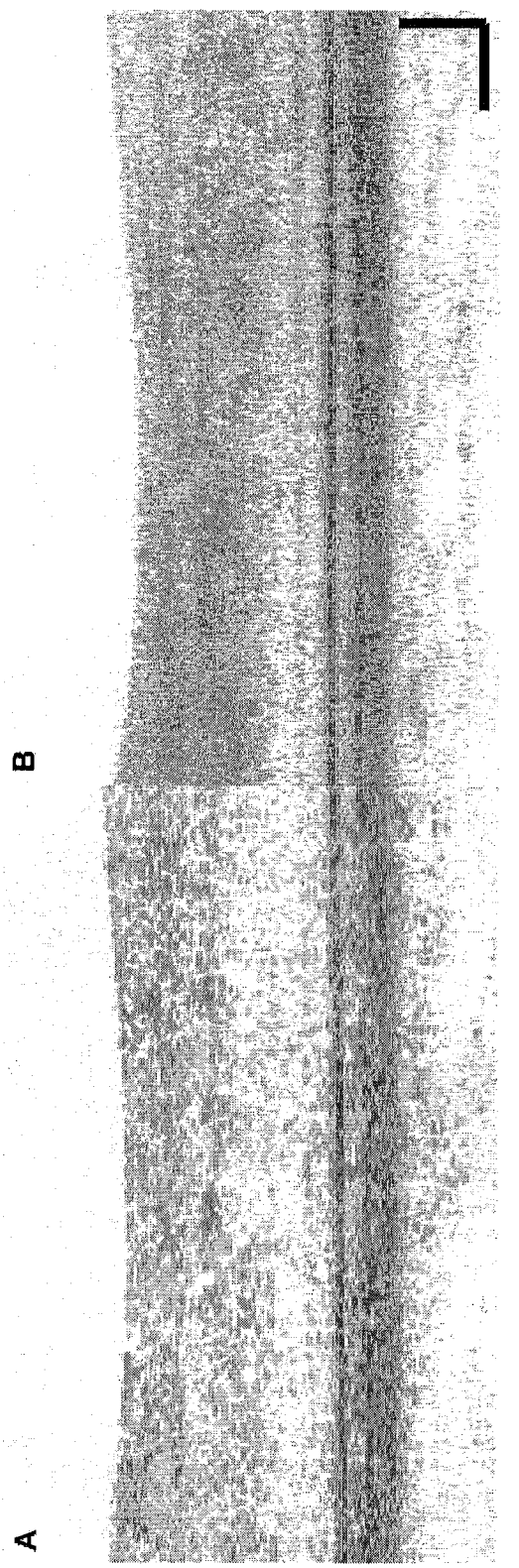
FIG. 6A shows an intensity image generated by an embodiment of an apparatus according to FIG. 1.
FIG. 6B shows an intensity image generated by an embodiment of an apparatus according to FIG. 1 excluding the adaptive optics.

In FIG. 6, two intensity images are compared, taken either with adaptive optics and a 6.0 mm beam incident on the eye (right), or without adaptive optics and a 1.2 mm beam (left). Data sets were taken under similar circumstances with equal amounts of power at the pupil (~350 µW), at the same eccentricity (1 degree superior—this location was chosen since it is close to the fovea but does not have a specular reflection occurring in the center of the image) and the same scan length (3 degrees or ~900 µm long). The average dynamic range within a data set of 100 images taken with a 1.2 mm beam was equal to 36 dB. For the data set taken with 6.0 mm and adaptive optics, the dynamic range averaged over 90 frames (the last 10 frames were lost due to eye motion) was equal to 39.0±1.2 dB. The focus of the Aoptix mirror was located at the inner plexiform layer for this particular data set. A higher dynamic range, up to 8 dB, can be obtained when the focus of the Aoptix mirror is positioned either on the RPE/photoreceptors, or on the retinal nerve fiber layer (at this location, there is no significant reflection returning from the nerve fiber layer). While capillaries can be seen in below the ganglion cell layer in the right image, they cannot be seen in the image taken without adaptive optics (left).

Example 5

Figure 7:
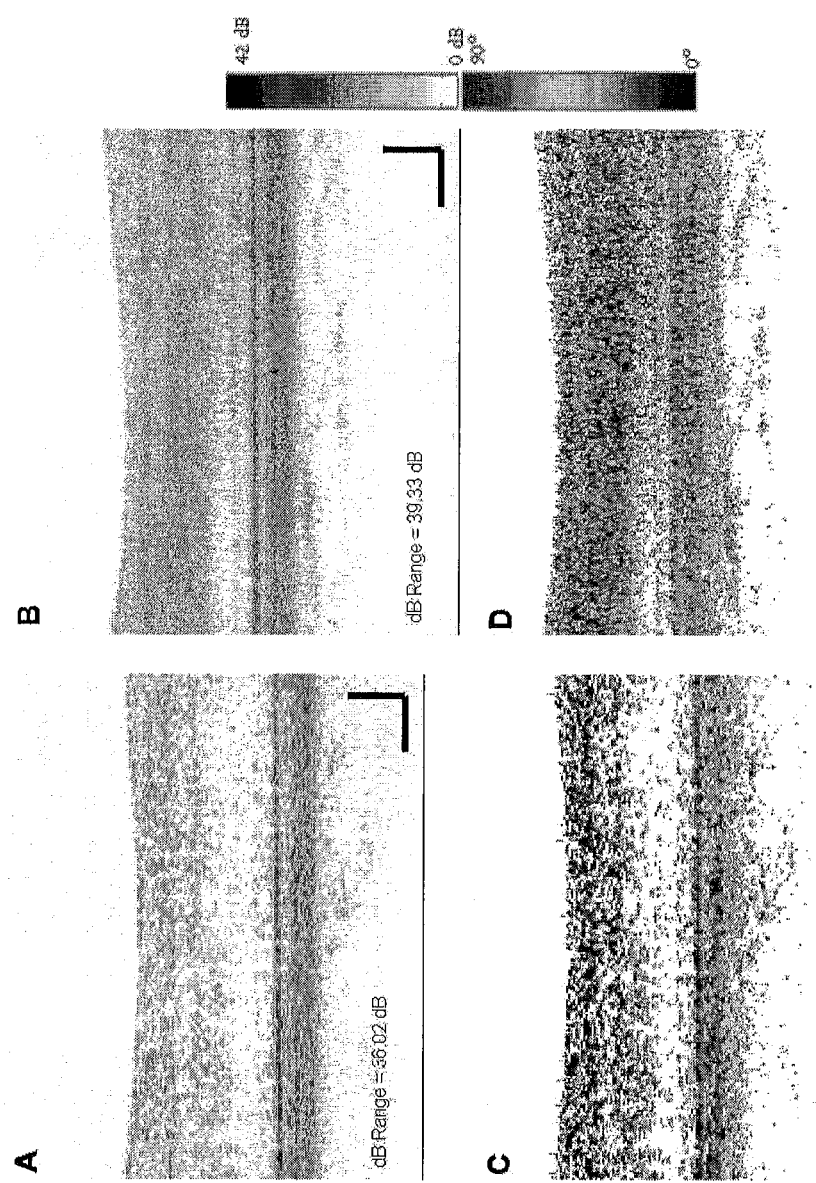
FIG. 7A shows an intensity image taken with an embodiment of the apparatus of FIG. 1 excluding adaptive optics.
FIG. 7B shows an intensity image taken with an embodiment of the apparatus of FIG. 1 including adaptive optics.
FIG. 7C shows a double pass phase retardation image taken with an embodiment of the apparatus of FIG. 1 but excluding adaptive optics.
FIG. 7D shows a double pass phase retardation image taken with an embodiment of the apparatus of FIG. 1 including adaptive optics.

A polarization-sensitive analysis was performed on the two data sets of FIG. 6, resulting in two sets showing both intensity and double pass phase retardation, as can be seen in FIG. 7. The double pass phase retardation images are false-color coded over 90°. Pixels with a low intensity have a less reliable double pass phase retardation value. During post-processing, the retardation data was masked with a thresholded intensity image, such that phase retardation pixels that are below an empirically determined intensity value were not displayed, to avoid spurious data points due to low intensity pixels. This intensity value was empirically determined, to avoid spurious double pass phase retardation points, i.e. isolated high phase retardation values at locations with low intensity. Stokes vectors were averaged for both data sets with a 2×2 moving average filter. Stokes vector averaging helps to diminish the effects of phase noise caused by speckle. To retrieve the phase retardation, surface Stokes vectors were compared with Stokes vectors at larger depths to calculate the double pass phase retardation Example 6

In both images of FIG. 7, a significant increase in retardation can be observed near the RPE layer, which is attributed to "depolarization" in the RPE. This effect referred to as fast axis scrambling. Fast axis scrambling causes a random distribution of Stokes vectors in the Poincaré sphere, creating an artifact in these phase retardation images that looks like high frequency spatial changes in phase retardation. In the right image, taken with a 6.0 mm beam and adaptive optics, a similar effect can be observed at the top of the connecting cilia. In the left image, due to a combination of a lower resolution and a larger speckle size, which leads to spatial averaging of Stokes vectors, fast axis scrambling cannot be seen near the connecting cilia.

Example 7

Figure 8:
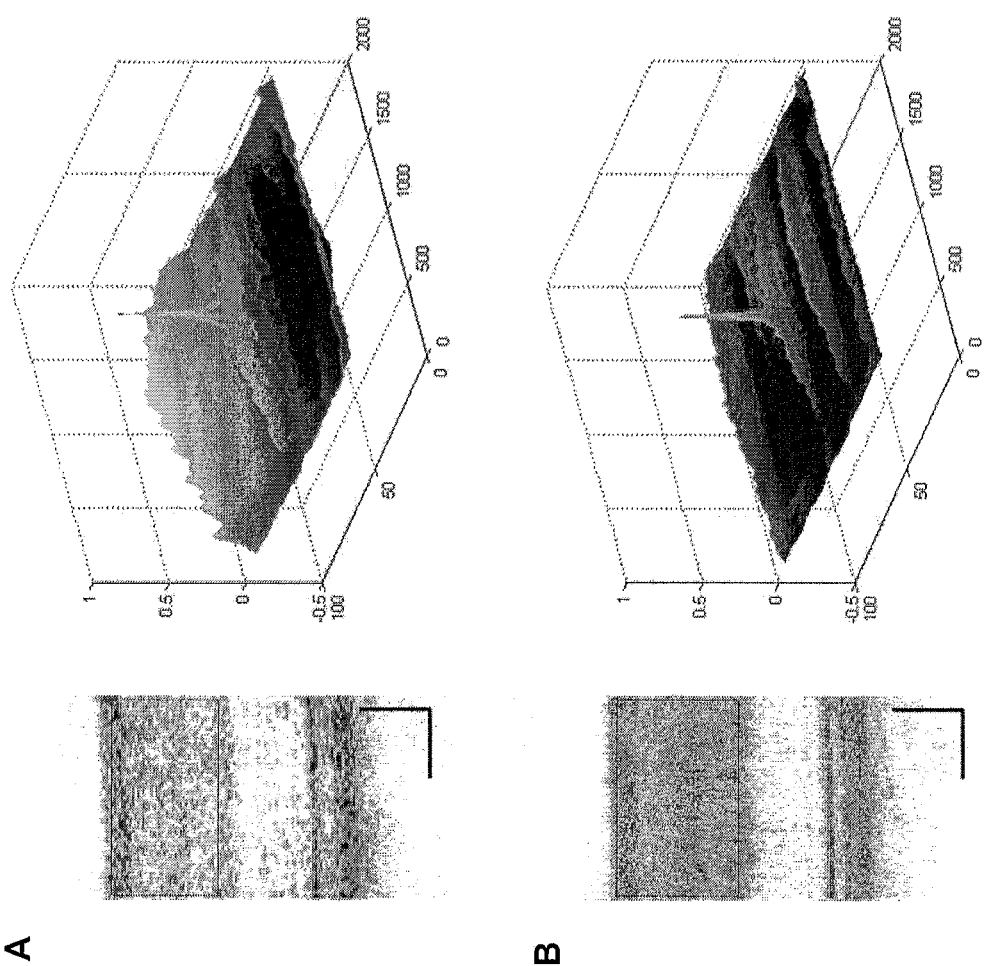
FIG. 8A shows a B-scan taken with a 1.2 mm beam (left) of an embodiment of FIG. 1 but excluding adaptive optics, and an auto-correlation plot of the area demarcated by a thin black line in the B-scan (right)
FIG. 8B shows a B-scan taken with a 6.0 mm beam (left) of an embodiment of FIG. 1 with adaptive optics, as well as an auto-correlation plot of the area demarcated by a thin black line in the B-scan (right).

Speckle analysis was performed on 10 B-scans of 1000 A-lines, covering 1 degree long patches, taken at 3 degrees superior in the same subject. In FIG. 8, two examples are given: without (left, 1.2 mm beam) and with (right, 6.0 mm beam) adaptive optics. Since the auto-correlation algorithm was sensitive to abrupt changes in intensity, only the upper retinal layers were used for speckle analysis. The areas that were analyzed are demarcated with a thin black line in FIG. 8. Additionally, for FIG. 8B, only the upper retinal layers were included in the analysis, because the auto-correlation algorithm was sensitive to abrupt changes in intensity. Using a two-dimensional auto-correlation algorithm in Matlab, averaging over 10 B-scans taken with a 1.2 mm beam, the FWHM speckle diameter, was equal to 14±1 µm, while the speckle diameter (FWHM) of B-scans taken with the 6.0 mm beam was equal to 3.1±0.1 µm. In depth, using amplitude-based B-scans, the width of a speckle was equal to 8±1 µm for the data taken with the 1.2 mm beam, and 7.3±0.3 µm for the data taken with the 6.0 mm beam. The differences in the magnitude of the standard deviation are caused by the larger uniformity in intensity of the AO B-scans. Furthermore, the dynamic range within the AO B-scans was approximately 6 dB larger than the dynamic range within the images taken with a 1.2 mm beam.

The coherence length of a 50 nm source in tissue is equal to approximately 6 µm (amplitude-based, FWHM). In both data a slightly larger speckle diameter in the vertical direction can be observed, although the auto-correlation was performed on an amplitude-based image. The difference is explained by slight variations in intensity as a function of depth. Within a single layer values between 5-7 µm are found.

The FWHM diffraction limited spot size of a 1.2 and 6.0 mm beam, respectively, are equal to 14 µm and 3.1 µm, respectively. Differences between these values and measured values (14±1 µm and 3.1±0.1 µm) are explained by differences in intensity as a function of width in B-scans and by the measurement error in the 1/e2 beam diameter measurement.

Example 8

A small percentage (~10%) of the light returning from the eye towards the interferometer was split towards the SHWS for AO purposes by means of a 90/10 pellicle beam splitter. Compared to a beam splitter cube, a pellicle beam splitter does not have a reflecting surface perpendicular towards the incident beam, so that specular reflections can be avoided. Since a SHWS is sensitive to back reflections a pellicle beam splitter is ideal for AO applications. The beam that passes through this thin beam splitter is shifted with respect to the incoming beam by only a few µm, while the chromatic dispersion is kept to a minimum. However, owing to its 90/10 splitting ratio, a pellicle beam splitter is highly diattenuating (only 50/50 or 60/40 beam splitters can be non-diattenuating). The detection scheme for birefringence measurements becomes less reliable when system parts are diattenuating.

The diattenuation of the system was minimized by positioning another diattenuating pellicle beam splitter close to the first one. While the first pellicle beam splitter directs ~10% of the light parallel to the optical table 184 towards the SHWS, the second beam splitter directs ~10% light perpendicular to the optical table 184 (see FIG. 1). Power measurements in our system indicated that diattenuation was negligible for the two controlled polarization states that were going towards the eye, while light that returned from the eye (which can be in any polarization state) could be diattenuated in a worst case by 0.03. The average angular displacement of a polarization state on the Poincaré sphere due to diattenuation is therefore equal to $(40*0.03)°=1.2°$. In comparison, the deviation due to Poisson noise (shot noise) at an SNR of an estimated 35 dB is equal to $\sqrt{(2/SNR)}$, or 0.03 radians, or 1.7°, demonstrating that the worst case diattenuation causes a deviation smaller than changes caused by Poisson noise. These deviations don't play a role in highly birefringent tissue that causes large amounts of retardation and therefore a large retardation angle in the Poincaré sphere, but can explain measured variations in tissue birefringence in thin tissue with a low birefringence.

The system contained a third pellicle beam splitter that was positioned in front of the eye, where a pupil camera was used to center the beam on the pupil. Before a measurement, this beam splitter was removed to avoid diattenuation.

Example 9

The method and algorithm used in the data analysis herein is described. In short, by using two transparent plates at any point in the system, two cavities were created, that generate a Fabry-Perot like signal, which shows up as two intensity modulations with different frequencies on top of the two orthogonal spectra. These two modulations were then used in the data analysis to perfectly overlap the two spectra.

Example 10

By using two dichroic mirrors in reflection for the OCT beam, the problem of diattenuation can be avoided (see FIG. 2). The OCT beam is inserted into the system after the Shack Hartmann wavefront sensor. For wavefront sensing purposes, we don't use the OCT light, but a separate beacon light (which can be a beam from a collimated laser, at low power, or an LED).

In order to optimize light efficiency, the dichroic beam splitter near the Shack Hartmann sensor reflects all OCT light, but transmits all beacon light. The beacon light in at least one embodiment has a center wavelength of ~700 nm, anything below the possible wavelengths for retinal imaging with OCT may be used, which ranges from ~700 nm to 1100 nm, but not visible to the human eye. As an example, a beacon with a center wavelength of 680 nm was used in an embodiment. This dichroic would pass all light with a wavelength shorter than 700 nm. The second dichroic, in front of the eye, would reflect both the beacon and the OCT light, but would transmit all visible light, so that we can use a target and a pupil camera. A dichroic that has a cutoff at 670 nm is acceptable, passing all visible light, but reflecting both the beacon light and the OCT beam.

While various embodiments of systems, devices, and methods for visualizing structures been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the spirit and scope of the present disclosure.

The invention claimed is:

1. A visualization apparatus, the apparatus comprising:
a source arm comprising a light source operable to emit a light beam, wherein the light beam defines a beam pathway;
a reference arm comprising a reflecting surface positioned within the beam pathway and capable of reflecting the light beam;
a sample arm comprising a wavefront sensor, an adaptive optics wavefront corrector, at least two 90/10 pellicles, and a target, wherein each of the wavefront sensor, the adaptive optics wavefront corrector, the at least two 90/10 pellicles, and target are positioned within the beam pathway, wherein the adaptive optics wavefront corrector is operable to compensate for at least one aberration in the light beam, wherein the at least two 90/10 pellicles are operable to reduce diattenuation of the apparatus via a first 90/10 pellicle of the at least two 90/10 pellicles that reflects about 10% of a first incident light beam directed at the first 90/10 pellicle parallel to a top surface of an optical table towards the wavefront sensor, and a second 90/10 pellicle of the at least two 90/10 pellicles that reflects about 10% of a second incident light beam directed at the second 90/10 pellicle perpendicular to the top surface of the optical table; and
a detector arm comprising a beam detector positioned within the beam pathway, wherein the beam detector is operable to detect the reflected light beam from the reference arm and light beam returning from the target;
wherein the visualization apparatus is operable to minimize at least one aberration from an optical element or the target.

2. The visualization apparatus of claim 1, wherein the light source is selected from a group consisting of white light sources, semiconductor sources, solid state lasers, spectrally-swept sources, and supercontinuum sources.

3. The visualization apparatus of claim 1, wherein the target is a portion of an eye.

4. The visualization apparatus of claim 3, wherein the portion of the eye is selected from a group consisting of a retinal tissue, a fundus tissue, a cornea, and a lens of an eye.

5. The visualization apparatus of claim 1, wherein the wavefront sensor is selected from a group consisting of a Hartmann-Shack wavefront sensor, a phase-shifting interferometer, a shearing interferometer, a pyramid sensor, a curvature sensor, a laser ray tracing, and a single photodetector.

6. The visualization apparatus of claim 1, wherein the adaptive optics wavefront corrector is a deformable mirror comprising a reflective surface bonded to an array of actuators.

7. The visualization apparatus of claim 6, wherein the array of actuators is selected from a group of about 20 or more, about 37 or more, about 100 or more, and about 144 or more piezo-electric actuators.

8. The visualization apparatus of claim 6, wherein the array of actuators are capable of adjusting the shape of the deformable mirror by at least 2 microns.

9. The visualization apparatus of claim 6, wherein the array of actuators are capable of adjusting the shape of the deformable mirror by at least 5 microns.

10. The visualization apparatus of claim 1, wherein the adaptive optics wavefront corrector corrects for a wavefront aberration.

11. The visualization apparatus of claim 1, wherein the adaptive optics wavefront corrector is selected from a group consisting of a bimorph mirror having two piezoelectric materials, a membrane mirror, a liquid crystal spatial light modulator, and a micro-opto-electro-mechanical system.

12. The visualization apparatus of claim 1, wherein the beam detector is selected from a group consisting of a CCD array camera, a complementary metal-oxide semiconductor array camera, a photodiode, a photodiode array, and an active pixel array.

13. The visualization apparatus of claim 1, wherein the sample arm further comprises a first dichroic beam splitter, and a second dichroic beam splitter.

14. The visualization apparatus of claim 1, wherein the detector arm further comprises a prism and a transmission grating, each positioned within the beam pathway.

15. The visualization apparatus of claim 1, further comprising a beam splitter operably coupled to the source arm, the reference arm, the sample arm, and the detector arm, wherein the beam splitter is capable of shunting a first portion of the light beam to the reference arm and a second portion of the light beam to the sample arm, wherein the first portion of the light beam returning from the reference arm and the second portion of the light beam returning from the sample arm are directed by way of the beam splitter to the detector arm.

16. The visualization apparatus of claim 15, wherein the beam splitter is operable to shunt a first portion of the source beam to the reference arm, the first portion of the source beam selected from the group consisting of at least about 90%, at least about 80%, at least about 70%, at least about 60%, at least about 50%, at least about 40%, and at least about 30% of the light beam.

17. The visualization apparatus of claim 15, wherein the beam splitter is operable to shunt a second portion of the light beam to the sample arm, the second portion of the light beam selected from the group consisting of at least about 70%, at least about 60%, at least about 50%, at least about 40%, at least about 30%, at least about 20%, and at least about 10% of the light beam.

18. The visualization apparatus of claim 1, wherein the source arm further comprises a calibration mechanism positioned within the beam pathway, the calibration mechanism operable to calibrate the light beam.

19. The visualization apparatus of claim 1, wherein the source beam further comprises an isolator, the isolator operable to prevent reflections of the light beam from interacting with the light source.

20. The visualization apparatus of claim 1, wherein the source arm further comprises a polarization modulator positioned within the beam pathway.

21. The visualization apparatus of claim 20, wherein the beam detector is synchronized with the polarization modulator.

22. The visualization apparatus of claim 1, wherein the reference arm further comprises at least one lens and a polarizer.

23. The visualization apparatus of claim 1, wherein the sample arm further comprises a first dichroic beam splitter in the beam pathway, a second dichroic beam splitter in the beam pathway, and a beacon operable to emit a beacon light in the beam pathway after the first dichroic beam splitter.

24. The visualization apparatus of claim 1, further comprising a processor, wherein the processor is operably coupled to the beam detector.

25. A visualization apparatus, the apparatus comprising:
a source arm comprising a light source operable to emit a light beam, an isolator, a polarization modulator, and a calibration mechanism, wherein the light beam defines a beam pathway;
a reference arm comprising a reflecting surface positioned within the beam pathway and capable of reflecting the light beam,
a sample arm comprising a wavefront sensor, an adaptive optics wavefront corrector, a first 90/10 pellicle, a second 90/10 pellicle, and a target, wherein each of the wavefront sensor, the first and second 90/10 pellicle, the adaptive optics wavefront corrector, and the target are positioned within the beam pathway, wherein the first 90/10 pellicle reflects about 10% of a first incident light beam directed at the first 90/10 pellicle parallel to a top surface of an optical table towards the wavefront sensor, wherein the second 90/10 pellicle reflects about 10% of a second incident light beam directed at the second 90/10 pellicle perpendicular to the top surface of the optical table, wherein both the first 90/10 pellicle and second 90/10 pellicle reduce diattenuation of the apparatus;
a detector arm comprising a prism, a transmission grating, and a beam detector, wherein each of the prism, transmission grating and beam detector are positioned within the beam pathway;
a beam splitter operably coupled to the source arm, the reference arm, the sample arm, and the detector arm, wherein the beam splitter is capable of shunting a portion of the light beam to the reference arm and the sample arm, wherein the portion of the light beams returning from the reference arm and sample arm are shunted by way of the beam splitter to the detector arm; and
a processor, wherein the processor is operably connected to the beam detector;
wherein the visualization apparatus is operable to generate a signal through interaction of the light beam emitted from the source arm and received by the detector arm;
wherein the visualization apparatus is operable to minimize at least one aberration from an optical element or the target; and
wherein the processor is operable to receive the signal.

26. The visualization apparatus of claim 25, wherein the adaptive optics wavefront corrector diminishes the at least one aberration produced by the target.

27. The visualization apparatus of claim 25, wherein the sample arm further comprises a first dichroic beam splitter in the beam pathway, a second dichroic beam splitter in the beam pathway, and a beacon operable to emit a beacon light in the beam pathway after the first dichroic beam splitter.

28. A visualization method, the method comprising:
measuring an at least one aberration in a target with a visualization apparatus, wherein the visualization apparatus comprises:
a source arm comprising a light source operable to emit a light beam, wherein the light beam defines a beam pathway;
a reference arm comprising a reflecting surface positioned within the beam pathway and capable of reflecting the light beam;
a sample arm comprising a wavefront sensor, at least two 90/10 pellicles, and an adaptive optics wavefront corrector, wherein each of the wavefront sensor, the at least two 90/10 pellicles, and the adaptive optics wavefront corrector are positioned within the beam pathway, wherein the adaptive optics wavefront corrector is operable to compensate for at least one aberration in the light beam; and
a detector arm comprising a beam detector positioned within the beam pathway, wherein the beam detector is operable to detect the reflected light beam from the reference arm and light beam returning from the target;
reducing diattenuation of the visualization apparatus by positioning a first of at least two 90/10 pellicles close to a second of at least two 90/10 pellicles, wherein the first of at least two 90/10 pellicles reflects about 10% of a first incident light beam directed at the first of at least two 90/10 pellicles parallel to a top surface of an optical table towards the wavefront sensor and the second of at least two 90/10 pellicles reflects about 10% of a second incident light beam directed at the second of at least two 90/10 pellicles perpendicular to the top surface of the optical table;
controlling the at least one aberration with the adaptive optics wavefront corrector to correct for the at least one aberration;
detecting the corrected light beam with the detector arm;
analyzing the detected light beam with a processor.

29. The visualization method of claim 28, wherein the step of analyzing the detected light beam eliminates birefringence and scattering properties of the target.

30. The visualization method of claim 28, wherein the step of analyzing the detected light comprises the steps of accumulating Stokes vectors, averaging the stokes vectors with re-alignment of the stokes vectors using a moving average filter to produce an averaged data set, and transmission of the averaged data set to an additional process, a storage medium, or a display medium.

31. The visualization method of claim 28, further comprising the step of displaying an image processed by the processor of the visualization apparatus by a display mechanism.

32. The visualization method of claim 28, wherein the visualization apparatus further comprises a quarter waveplate.

33. The visualization method of claim 28, wherein the step of analyzing the detected light utilizes Jones matrix calculations to retrieve polarization properties.

\* \* \* \* \*